(12) United States Patent
Benade et al.

(10) Patent No.: US 8,246,697 B2
(45) Date of Patent: Aug. 21, 2012

(54) MIXTURE OF AMIDES AND COSMETIC COMPOSITIONS COMPRISING SAID MIXTURE

(75) Inventors: Jürgen Benade, Emmerich (DE); Reinout Van Der Veen, Emmerich (DE); Neus Subirats Vicient, Barcelona (ES); Pilar Castán Barberán, Barcelona (ES)

(73) Assignee: KAO Corporation S.A. (ES)

( * ) Notice: Subject to any disclaimer, the term of this patent is extended or adjusted under 35 U.S.C. 154(b) by 0 days.

(21) Appl. No.: 13/141,931

(22) PCT Filed: Dec. 23, 2009

(86) PCT No.: PCT/EP2009/067854
§ 371 (c)(1), (2), (4) Date: Sep. 13, 2011

(87) PCT Pub. No.: WO2010/072810
PCT Pub. Date: Jul. 1, 2010

(65) Prior Publication Data
US 2012/0005843 A1    Jan. 12, 2012

(30) Foreign Application Priority Data
Dec. 24, 2008 (EP) .................................. 08382088

(51) Int. Cl.
*A61Q 5/10* (2006.01)
(52) U.S. Cl. ............. 8/405; 8/406; 8/431; 8/435; 8/586; 8/590; 8/602; 8/604; 8/609
(58) Field of Classification Search .............. 8/405, 406, 8/431, 435, 586, 590, 602, 604, 609
See application file for complete search history.

(56) References Cited

U.S. PATENT DOCUMENTS
2005/0235430 A1* 10/2005 Denzer et al. .................... 8/405

FOREIGN PATENT DOCUMENTS
| | | |
|---|---|---|
| EP | 0 176 151 A1 | 4/1986 |
| EP | 1 340 489 A1 | 9/2003 |
| WO | 01/78668 A1 | 10/2001 |
| WO | 02/36082 A2 | 5/2002 |

OTHER PUBLICATIONS

STIC Search Report dated Dec. 14, 2011.*
Extended European Search Report dated Jun. 24, 2009 of related Application No. EP 08382088.6-1521 (6 pages).

* cited by examiner

*Primary Examiner* — Eisa Elhilo
(74) *Attorney, Agent, or Firm* — Barnes & Thornburg LLP

(57) ABSTRACT

A mixture of amides of the following formula (I) is disclosed wherein —$R_1$ represents a hydrogen atom or an alkyl group having 1 to 5 carbon atoms; —$R_2$ and $R_3$ represent independently, a hydrogen atom or a linear or branched alkyl group having 1 to 5 carbon atoms which is optionally hydroxylated, provided that $R_2$ and $R_3$ are not a hydrogen atom at the same time; -n has a value in the range of 0.2 to lower than 3; characterized in that said mixture comprises: -amides (a) of formula (I) wherein R represents a $C_6$-$C_{24}$ alkyl or alkenyl group having even number of carbon atoms and at least a 95 wt. % of linearity; and -amides (b) of formula (I) wherein R represents a $C_5$-$C_{23}$ alkyl or alkenyl group having odd or odd and even number of carbon atoms and a 35-85 wt. % of linearity; and cosmetic compositions comprising said mixture, particularly dying compositions.

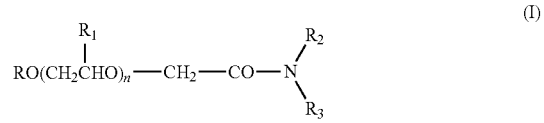

(I)

20 Claims, No Drawings

ND COSMETIC
MIXTURE OF AMIDES AND COSMETIC COMPOSITIONS COMPRISING SAID MIXTURE

CROSS-REFERENCE TO RELATED APPLICATIONS

This application is a U.S. national counterpart application, filed under 35 U.S.C. §371, of International Application Serial No. PCT/EP2009/067854 filed Dec. 23, 2009, which claims priority to EP Application Serial No. 08382088.6 filed Dec. 24, 2008, the disclosures of both of which applications are hereby incorporated herein by reference in their entirety.

TECHNICAL FIELD

The present invention relates to a mixture of specific amides and to cosmetic compositions comprising said mixture, particularly dying compositions.

PRIOR ART

A "cosmetic product" is considered as any substance or composition intended to be placed in contact with the various external parts of the human body (epidermis, hair system, nails, lips and external genital organs) or with the teeth and the mucous membranes of the oral cavity with a view exclusively or mainly to cleaning them, perfuming them, changing their appearance and/or correcting body odours and/or protecting them or keeping them in good condition.

According to the invention, the term "cosmetic composition" (or cosmetic formulation) mean any cosmetic product or preparation of the type described in Annex I ("Illustrative list by category of cosmetic products") of the Council Directive of the European Communities No. 76/768/EEC of Jul. 27, 1976, known as the Cosmetics Directive.

The cosmetic compositions can be formulated in a large number of types of product for the skin and/or the hair such as mousses, gels (in particular styling gels), masks for the face or the hair, conditioners, formulations for improving hairstyling, or for facilitating the combing or disentangling of the hair, for providing volume or sheen, rinsing formulations, compositions for dying or colouring the hair, hand and body lotions and oils, products for improving the moisturization of the skin, cleansing milks, make-up-removing compositions, creams or lotions for protecting against the sun and ultraviolet radiation, care and/or treatment milks and creams, anti-acne preparations, local analgesics, mascaras, products intended to be applied to the lips or other mucous membranes, sticks, deodorant and antiperspirant products, shaving lotions, bath oils, talcs and other compositions of the same type.

On the other hand, it is known for centuries to dye keratinous fibres, for example human hair, with dyeing compositions comprising dyes or dye precursors.

Most hair colouring products fall under three major groupings:
1. Temporary hair colour
2. Semi permanent hair colour
3. Permanent hair colour.

Temporary hair colour is a leave on product that causes minimal damage to the hair. However, temporary hair colour causes stains, and leaches out under rain or with perspiration. Temporary hair colour washes out with the next shampoo. They are normally formulated with water-soluble direct dyes complexed with cationic surfactants to give a fine dispersion with particle sizes too great to penetrate through the cuticle into the cortex. As a result, the dye complex is deposited on the surface of the hair, from which it is easily removed by shampoo. Temporary hair colour also does not give any control to the consumer over the amount of colour deposited or the permanency of the colour supplied. Temporary hair colour does not result in a wide variety of colours and it has only a limited appeal.

Semi-permanent hair colour comes as a rinse, and it causes minimal damage to the hair. However, semi-permanent hair colour washes out to some degree with each shampoo and washes out completely within about 4 to 6 shampoos. Semi permanent hair colour employ low molecular weight dyes, which normally are simple derivatives of nitroanilines, nitrophenyldiamines, and nitroaminophenols, supplemented by a few azo and anthraquinone dyes. These dyes are of low enough molecular weight to penetrate into the cuticle and partially into the cortex of the hair. As a result, they are somewhat resistant to shampooing. Semi permanent hair colour does not give the consumer any control regarding the amount of colour deposited or the permanency of the colour.

Permanent hair colour generally comes in two parts: a dye solution and a developer solution. Permanent hair colour compositions do not contain dyestuffs in the conventional sense of the word. They contain colourless precursors which will react with an oxidizing agent inside the hair fibre to produce coloured molecules. Because of the damaging nature of conventional permanent dye treatments, most home permanent hair colouring products come with a post treatment conditioner. In a permanent hair colouring treatment, the dye solution and the developer solution, which contains an oxidizing agent (normally hydrogen peroxide), are mixed and then applied to the hair, which is then left for about 15 to about 35 minutes. The hair is then rinsed with water, treated with a post treatment conditioner, and then rinsed again with water.

The preparations for dyeing keratinous fibres often contain various reagents in addition to dyes. The purpose of these reagents is, in many cases, to control the manner in which dyes are adsorbed on the fibres and hence to control the evenness of the final dyeing, i.e. to produce a uniform distribution of the dyestuff.

These compounds, collectively referred to as "levelling agents", may be inorganic salts such as sodium sulphate, although various types of surfactants were found to be more effective. Anionic, cationic or amphoteric surfactants are commonly used, either alone or in blends, for dyeing both human and animal keratinous fibres. The mode of action of these levelling agents, especially the surfactants, usually involves formation of a complex with the dye. The complex is adsorbed more evenly by the fibres than the dye alone.

Improved evenness of dye adsorption is particularly important when dyeing damaged fibres in order to avoid an undesired appearance in the final dyed fibres, and thus surfactant-levelling agents are generally employed when dyeing damaged fibres. The damage to the fibres can be produced by repeated dyeing to such an extent that the tip and root portions of the fibres have markedly different dyeing properties. The above-mentioned undesired appearance refers to an undesired speckled effect arising from differences in colour between adjacent fibres or portions of the same, an effect often associated with damaged keratinous fibres.

It is desired to achieve the above-mentioned requirement of producing a uniform distribution of the dyestuff without losing the intensity of the hair colouring while obtaining optimal colour results (adequate colouring of some type of keratinous fibres).

Furthermore, a hair-dyeing product should be able to be confined upon application to the hair so that, on the one hand, it does not run over the face or outside the areas which it is desired to dye, and, on the other hand, a uniform and regular colouration may be obtained on the hair as a whole. Compositions comprising oxidation dye(s) prior to combining with an oxidizing agent should also be stable over time, such as, for example, from the rheological point of view.

Traditional thickeners, which can provide a gelling effect when diluted by water and/or surfactants, have been used conventionally to localize the dye product as applied on hair, so that the dye product does not touch the face or the area outside the area to be dyed. Such thickeners, chosen as appropriate, for example include crosslinked polyacrylic acid, hydroxyethylceiluloses, certain polyurethanes, waxes or mixtures of nonionic surfactants.

Commonly, fatty acid alkanolamides, optionally alkoxylated, like stearic acid mono- and diethanolamide (Stearamide MEA and Steramide DEA), coconut fatty acid mono- and diethanolamide (Cocamide MEA and Cocamide DEA), have been used in compositions for dyeing keratinous fibres, especially human hair as thickening agents or agents for adjusting the rheology.

DE-A-19701422 describes aqueous hair dyeing compositions with improved emulsion ability, consistency and colour intensity. Said aqueous hair dyeing compositions contain an oxidation dye precursor and 0.25-5 wt. % of an ethoxylated $C_{10}$-$C_{20}$ fatty acid alkanolamide. Preferably the hair colour compositions contain 0.5-2.5 wt. % PEG-5 Cocamide. It is stated that replacing PEG-5 Cocamide by PEG-3 Cocamide, PEG-7 Cocamide, PEG-3 Lauramide, PEG-6 Lauramide, PEG-9 Oleamide, PEG-4 Rapeseedamide and PEG-4 Stearamide similar improvements in the colour quality can be obtained.

WO-A-03053329 describes composition for dyeing hair, comprising, in a medium suitable for dyeing, at least an oxidation dye and more than 5 wt. % of the composition of at least an oxyethylene rapeseed fatty acid amide, preferably PEG-4 Rapeseedamide.

On the other hand, cosmetic compositions comprising polyoxyethylene alkyl ether carboxylic acid monoethanolamides are known. The international patent application WO-A-WO0236082 describes optically transparent aqueous compositions containing hydrophobic silicone oil, b) a solubilizer for the silicone oil, and (c) an anionic surfactant; said compositions being suitable as a hair treatment composition such as a shampoo. Among the preferred solubilizers for the silicone oil Trideceth-2 Carboxamide MEA is mentioned.

$C_{13}$-$C_{15}$ alkyl ether carboxylic acid monoethanolamide containing 2 moles of ethylene oxide (polyoxyethylene (2) $C_{13}$-$C_{15}$ alkyl ether carboxylic acid monoethanolamide) is also known in hair dyeing compositions as described in WO-A-0178668, EP-A-1279395, EP-A-1321133, EP-A-1321134, EP-A-1321135 and EP-A-1329216 and in the International patent application WO-A-03072073. Said $C_{13}$-$C_{15}$ alkyl ether carboxylic acid monoethanolamide may have a highly branched alkyl chain (linearity around 50%) as described in WO-A-0178668. Although said monoethanolamide is a good thickening agent (agent for adjusting the rheology), its levelling effect is not completely acceptable.

Additionally, WO-A-03072073 also describes $C_{12}$-$C_{14}$ alkyl ether carboxylic acid monoethanolamides containing 3 moles of ethylene oxide (polyoxyethylene (3) $C_{12}$-$C_{14}$ alkyl ether carboxylic acid monoethanolamide); 4.5 moles of ethylene oxide (polyoxyethylene (4.5) $C_{12}$-$C_{14}$ alkyl ether carboxylic acid monoethanolamide); and 7 moles of ethylene oxide (polyoxyethylene (7) $C_{12}$-$C_{14}$ alkyl ether carboxylic acid monoethanolamide) in hair dyeing compositions. Although some of said monoethanolamides present good levelling effect (especially the ones containing 4.5 and 7 moles of ethylene oxide), their theological behaviour is not comparable to the $C_{13}$-$C_{15}$ alkyl ether carboxylic acid monoethanolamide type.

SUMMARY OF THE INVENTION in the field of hair dyeing compositions, there exists a need for dyeing compositions containing improved levelling agents that make the colour of the dyed fibres more uniform, provide intense and chromatic shades of low selectivity and good fastness, while offering good stability of the compositions, good ease of application leading to uniform and regular colourations of the hair and a good cosmetic condition to the treated hair.

The authors of the present invention have surprisingly found that the mixture of amides according to the invention can provide similar or improved theological and levelling properties compared to the amides already known in the art.

It is thus the object underlying the present invention a mixture of amides of the following formula (I)

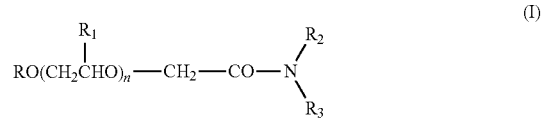

wherein $R_1$ represents a hydrogen atom or an alkyl group having 1 to 5 carbon atoms;

$R_2$ and $R_3$ represent independently, an hydrogen atom or a linear or branched alkyl group having 1 to 5 carbon atoms which is optionally hydroxylated, provided that $R_2$ and $R_3$ are not an hydrogen atom at the same time;

n has a value in the range of 0.2 to lower than 3;

characterized in that said mixture comprises:

amides (a) of formula (I) wherein

R represents a $C_6$-$C_{24}$ alkyl or alkenyl group having even number of carbon atoms and at least a 95 wt. % of linearity; and amides (b) of formula (I) wherein R represents a $C_5$-$C_{23}$ alkyl or alkenyl group having odd or odd and even number of carbon atoms and a 35-85 wt. % of linearity.

The present invention also provides a cosmetic composition comprising a mixture of amides according to the invention.

In particular, the present invention provides dyeing compositions comprising a) a dyestuff; and b) a mixture of amides, said mixture comprising, based on the total amount of the amide mixture:

i) 5-100 wt. % of amides (a) as defined in claims 1 to 8 ii) 0-95 wt. % of amides (b) as defined in claims 1 to 8.

The present invention also provides a method for dyeing keratinous fibres with the dyeing compositions of the invention.

The present invention also provides the use of a mixture of amides according to the invention as levelling agent in compositions for dyeing of keratinous fibres, especially human hair.

The present invention also provides the use of a mixture of amides according to the invention as thickening agents in compositions for dyeing of keratinous fibres, especially human hair.

DESCRIPTION OF THE INVENTION

The Mixture of Amides

According to the invention, it is preferred that in the mixture of amides of the following formula (I)

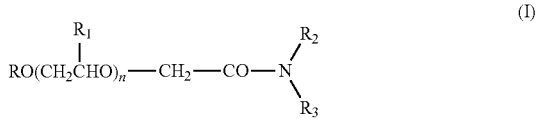

$R_1$ represents a hydrogen atom or an alkyl group having 1 to 2 carbon atoms, preferably a hydrogen atom or a methyl group, more preferably a hydrogen atom;

$R_2$ and $R_3$ represent independently, a hydrogen atom or an hydroxylated alkyl group having 1 to 5 carbon atoms selected from the group consisting of hydroxymethyl, hydroxyethyl, n-hydroxypropyl, iso-hydroxypropyl, n-hydroxybutyl, iso-hydroxybutyl, tert-hydroxybutyl and n-hydroxypentyl, preferably hydroxyethyl, n-hydroxypropyl, iso-hydroxypropyl; provided that $R_2$ and $R_3$ are not a hydrogen atom at the same time. It is even more preferred that $R_2$ represents a hydrogen atom or an hydroxyethyl group and $R_3$ represents an hydroxyethyl, n-hydroxypropyl or iso-hydroxypropyl group;

n has a value in the range of 0.2 to lower than 3, preferably in the range of 0.5 to 2.5, more preferably in the range of 1 to 2;

According to the invention, it is also preferred that in the amides (a) of formula (I) R represents a $C_8$-$C_{18}$ alkyl or alkenyl group, preferably a $C_{10}$-$C_{14}$ alkyl or alkenyl group, having even number of carbon atoms and at least a 98 wt. % of linearity.

According to the invention, it is also preferred that in the amides (b) of formula (I) R represents a $C_5$-$C_{17}$ alkyl or alkenyl group, preferably a $C_9$-$C_{15}$ alkyl or alkenyl group having odd or odd and even number of carbon atoms and a 40-75 wt. % of linearity, preferably a 45-70 wt. % of linearity.

In the event that amide (b) contains molecules with linear alkyl or alkenyl groups of an even number of carbon atoms, such molecules are considered to belong to amide (a) for the calculation of the respective weights, even though they may be derived from oxo-alcohols.

According to the invention, it is preferred that in the amides (a) or (b) of formula (I), $R_1$ represents an hydrogen atom, $R_2$ represents an hydrogen atom and $R_3$ represents an hydroxyethyl group.

According to the invention, in the mixture of amides of formula (I), the weight ratio of amides (a) to amides (b) is in the range of 1:10 to 10:1, preferably in the range of 1:5 to 5:1, even more preferably 1:3 to 1:1.

A particularly preferred mixture of amides is those according to formula (II)

wherein $R_4$ represents an hydroxyethyl, n-hydroxypropyl or iso-hydroxypropyl group, n has a value in the range of 0.2 to lower than 3, preferably in the range of 0.5 to 2.5, more preferably in the range of 1 to 2;

said mixture comprising:

amides (a) of formula (II) wherein

R represents a $C_6$-$C_{24}$, preferably a $C_8$-$C_{18}$, more preferably a $C_{10}$-$C_{14}$ alkyl or alkenyl group having even number of carbon atoms and at least a 95 wt. % of linearity, preferably at least a 98 wt. % of linearity; and amides (b) of formula (II) wherein R represents a $C_5$-$C_{23}$, preferably a $C_5$-$C_{17}$, more preferably a $C_9$-$C_{15}$ alkyl or alkenyl group having odd or odd and even number of carbon atoms and a 40-85 wt. % of linearity, preferably a 45-75 wt. % of linearity, even more preferred a 55-75 wt. % of linearity.

The amides of formula (I) or formula (II) can be prepared in an usual manner, as mentioned in the Swiss patent application CH-A-411221, starting from the corresponding alkyl ether carboxylic acid. A suitable method of preparation is heating the free alkyl ether carboxylic acid with the suitable amine and distilling off water.

On the other hand, alkyl ether carboxylic acids are usually obtained by alkoxylation and subsequent carboxymethylation of alcohols.

The process is divided into two steps. The first one is the alkoxylation of alcohols under standard conditions known by the skilled in the art. For instance, the polyoxyethylene group is obtained by addition of ethylene oxide to the suitable alcohols, mostly with an alkaline catalyst such as NaOH, KOH or $NaOCH_3$, giving a broad polyoxyethylene oxide distribution (broad ethoxylation degree). For special applications the ethoxylation can be catalyzed by Lewis acids or by using metallic Na or NaH to achieve a narrow range distribution (narrow ethoxylation degree). However, one may also start from commercially available ethoxylated alcohols.

In the second step, the ethoxylated alcohols are reacted with a strong base, like sodium or potassium hydroxide, in presence of a reducing agent, i.e. sodium borohydride, to obtain the corresponding alkoxylate, which is carboxymethylated with sodium monochloroacetate (SMCA).

The amides (a) of formula (I) or (II) are derived from natural alcohols obtained from vegetable oils and fats such those obtained from castor oil, coconut oil, corn oil, mustard oil, olive oil, palm oil, peanut oil, rapeseed oil, sunflower oil, soybean oil, tall oil, etc., as well as purified fatty alcohols, like caproic alcohol, caprylic alcohol, capric alcohol, lauric alcohol, myristic alcohol, palmitic alcohol, palmoleic alcohol, stearic alcohol, isostearic alcohol, oleic alcohol, elaidinic alcohol, petroselenic alcohol, linoleic alcohol, linolenic alcohol, eleostearic alcohol, ricinoleic alcohol, arachidic alcohol, gadoleic alcohol, behenic alcohol, erucic alcohol, or their technical-grade mixtures.

The amides (b) of formula (I) or (II) are derived from synthetic alcohols (oxo-alcohols) obtained from the petrochemical industry.

The preparation of the so called oxo-alcohols is known in the art. One typical method of preparing such oxo-alcohols is by hydroformylating an olefin into an oxo-aldehyde followed by hydrogenation of this oxo-aldehyde into the oxo-alcohol. Hydroformylation is typically conducted in the presence of a homogeneous catalyst which is based on a source of a transition metal, typically a metal of Group 8 (iron, ruthenium or osmium), 9 (cobalt, rhodium or iridium) or 10 (nickel, palladium or platinum) of the Periodic Table of Elements.

In their catalytically active form these metals may be used with carbonyl ligands, but they can also be used as a complex with other ligands, suitably phosphorus-containing ligands. Such catalysts are commonly referred to as phosphine and/or phosphite-modified hydroformylation-catalysts.

The secondary reaction, i.e. the hydrogenation of the oxo-aldehyde into the corresponding oxo-alcohol, occurs simultaneously with the actual hydroformylation reaction.

Some of the homogeneous hydroformylation catalysts are sufficiently active to hydrogenate the in-situ formed oxo-aldehyde into the desired oxo-alcohol. Sometimes, however, a separate hydrofinishing step is applied in order to improve the quality of the final oxo-alcohol product in terms of its aldehyde content.

Throughout this specification the linearity of R in the amides (a) and in the amides (b) of formula (I) or formula (II) is defined according to the linearity of the starting alcohols (natural alcohols for the amides (a) and oxo-alcohols for the amides (b)), as the weight percentage of linear primary alcohols relative to the total amount of alcohols.

In a preferred embodiment, the mixture of amides (a) and (b) according to the invention is obtained by mixing suitable natural alcohols with suitable oxo-alcohols, alkoxylating said mixture and subsequently carboxymethylating the alkoxylated alcohols to obtain the corresponding alkyl ether carboxylic acid, which is finally heated with a suitable amine.

In another embodiment, the mixture of amides (a) and (b) according to the invention is obtained by mixing suitable alkoxylated natural alcohols with suitable alkoxylated oxo-alcohols, carboxymethylating said mixture of alkoxylated alcohols to obtain the corresponding alkyl ether carboxylic acid, which is finally heated with a suitable amine.

Alternatively, the mixture of amides (a) and (b) according to the invention is obtained just by mixing the amides (a) and amides (b) which have been prepared independently.

The Cosmetic Compositions

The present invention also provides a cosmetic composition comprising a mixture of amides according to the invention.

It is preferred that said mixture of amides is present in quantities of 0.05% to 25%, 0.1% to 25%, preferably 0.25% to 20%, even more particularly 0.5% to 15% by weight, based on the cosmetic composition. These cosmetic compositions generally contain, in addition to the mixture of amides according to the invention, anionic, cationic, non-ionic or amphoteric surfactants, or mixtures thereof.

These additional surfactants are generally present so that the total amount of surfactants does not exceed 40 wt. %. The preferred total amount is in the range of 10 to 35 wt. %.

The cosmetic compositions are, for example:
Creams, emulsions, lotions, gels and oils for the skin (hands, face, feet, etc.)
Face masks
Tinted bases (liquids, pastes, powders)
Make-up powders, after-bath powders, hygienic powders, etc.
Toilet soaps, deodorant soaps, etc,
Perfumes, toilet waters and eau de Cologne
Bath and shower preparations (salts, foams, oils, gels, etc.)
Depilatories
Deodorants and antiperspirants
Hair care products:
  hair tints (hair dyeing compositions) and bleaches,
  products for waving, straightening and fixing,
  setting products,
  cleansing products (lotions, powders, shampoos),
  conditioning products (lotions, creams, oils),
  hairdressing products (lotions, lacquers, brilliantines)
Shaving products (creams, foams, lotions, etc.)
Products for making up and removing make-up from the face and the eyes.
Products intended for application to the lips
Products for care of the teeth and the mouth
Products for nail care and make-up
Products for external intimate hygiene
Sunbathing products
Products for tanning without sun
Skin-whitening products
Anti-wrinkle products.

Examples of these additional surfactants include the following:

Anionic Surfactants

Typical examples of anionic surfactants are soaps, preferably $C_{12}$-$C_{18}$ fatty acid soaps, like soaps derived from lauric acid, myristic acid, palmitic acid, stearic acid, isostearic acid, oleic acid or linoleic acid. Said soaps contain an appropriate cation, selected from the group consisting of an alkali metal, an alkaline earth metal, ammonium, an alkylammonium, an alkanolammonium or a glucammonium. Preferably the cation group is selected from the group consisting of sodium, potassium and triethanolamine. Preferred $C_{12}$-$C_{18}$ fatty acid soaps include triethanolamine stearate, triethanolamine palmitate, triethanolamine myristate, triethanolamine laurate, sodium stearate, sodium palmitate, sodium myristate, sodium laurate, potassium stearate, potassium palmitate, potassium myristate, and potassium laurate.

Other examples of anionic surfactants are alkylbenzenesulfonates, alkanesulfonates, olefin sulfonates, alkylether sulfonates, glycerol ether sulfonates, α-methyl ester sulfonates, sulfofatty acids, alkylsulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, amide ether carboxylic acids and salts thereof, fatty acid isethionates, fatty acid sarcosinates, fatty acid taurides, N-acylamino acids such as, for example, acyl lactylates, acyl tartrates, acyl glutamates, acyl aspartates, alkyl oligoglucoside sulfates, protein fatty acid condensates (particularly wheat-based vegetable products) and alkyl (ether) phosphates.

Cationic Surfactants

Typical examples of cationic surfactants are amine salts, quaternary ammonium salts (quats) like monoalkyl dimethyl amine derivatives, dialkyl monomethyl amines and imidazoline derivatives, and the quaternized derivatives of polyalkanolamine esters (esterquats). Examples of commercially available quats are: QUARTAMIN® AB (Behentrimonium Chloride), QUARTAMIN® 60W25 (Cetrimenium Chloride) and QUARTAMIN® ABK (Behentrimonium Chloride and Cetearyl Alcohol), all marketed by KAO Corporation S.A.

Examples of commercially available esterquats are QUARTAMIN® BTC-131 (Behenoyl PG-Trimonium Chloride), marketed by KAO Chemicals GmbH, and TETRANYL® CO-40 (Dioleoylethyl Hydroxyethylmonium Methosulfate and Dipropylene Glycol) marketed by KAO Corporation S.A.

Non-Ionic Surfactants

Specific examples of non-ionic surfactants are alkoxylated trimethyolol propane, alkoxylated 1,2,3-trihydroxy hexane, alkoxylated pentaetrythritol, alkoxylated sorbitol, alkoxylated glycerol fatty acid ester, alkoxylated trimethyolol propane fatty acid ester, alkoxylated 1,2,3-trihydroxy hexane fatty acid ester, alkoxylated pentaetrythritol fatty acid ester, alkoxylated sorbitol fatty acid ester, fatty alcohol polyglycol ethers, alkylphenol polyglycol ethers, fatty acid polyglycol esters, fatty acid amide polyglycol ethers, fatty amine polyglycol ethers, mixed ethers and mixed formals, optionally partly oxidized alk(en)yl oligoglycosides or glucuronic acid derivatives, fatty acid-N-alkylglucamides, protein hydrolyzates (particularly wheat-based vegetable products), polyol fatty acid esters, sugar esters, alkyl polyglucosides, sorbitan esters, and polysorbates. and alkanolamides, including alkoxylated alkanolamides, preferably ethoxylated alkanolamides derived from rapeseed oil.

Amphoteric Surfactants

Specific examples of amphoteric surfactant are alkyl amine oxides, alkyl betaines, alkyl sulphobetaines (sultaines), amidoalkyl betaines, alkyl glycinates, alkyl carboxyglycinates, alkyl amphoacetates, alkyl amphopropionates, alklylamphoglycinates, alkyl amidopropyl betaines, alkyl amidopropyl- and hydroxysultaines. Particularly preferred amphoteric surfactants are alkyl amine oxides, alkyl sulphobetaines (sultaines), alkylamphoglycinates and alkyl amphoacetates such as sodium coco monoamphoacetate or sodium coco diamphoacetate, and alkyl amidopropyl betaines such as cocoamido propyl betaine.

Other Components

These cosmetic compositions may also contain mild surfactants, oil components, superfatting agents, pearlizing waxes, consistency factors, thickeners, polymers, silicone compounds, fats, waxes, stabilizers, biogenic agents, deodorizers, anti-dandruff agents, film farmers, swelling agents, UV protection factors, antioxidants, hydrotropes, preservatives, insect repellents, self-tanning agents, solubilizers, perfume oils, dyes, germ inhibitors and the like as further auxiliaries and additives.

Co-Emulsifiers

Suitable co-emulsifiers are, for example, nonionic surfactants from at least one of the following groups:

(1) products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group;

(2) ethoxylated glycerides as described in the European patent applications EP-A-0586323 and EP-A-1045021, preferably obtained by reaction of triglycerides, glycerine and ethylene oxide;

(3) glycerol monoesters and diesters and sorbitan monoesters and diesters of saturated and unsaturated fatty acids containing 6 to 22 carbon atoms and ethylene oxide odducts thereof;

(4) alkyl mono- and oligoglycosides containing 8 to 22 carbon atoms in the alkyl group and ethoxylated analogs thereof;

(5) products of the addition of 15 to 60 moles of ethylene oxide onto castor oil and/or hydrogenated castor oil;

(6) polyol esters and, in particular, polyglycerol esters such as, for example, polyglycerol polyricinoleate, polyglycerol poly-12-hydroxy-stearate or polyglycerol dimerate isostearate. Mixtures of compounds from several of these classes are also suitable;

(7) products of the addition of 2 to 15 moles of ethylene oxide onto castor oil and/or hydrogenated castor oil;

(8) partial esters based on linear, branched, unsaturated or saturated $C_6$-$C_{22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(9) mono-, di- and trialkyl phosphates and mono-, di- and/or tri-PEG-alkyl phosphates and salts thereof;

(10) wool wax alcohols;

(11) polysiloxane/polyalkyl polyether copolymers and corresponding derivatives;

(12) mixed esters of pentaerythritol, fatty acids, citric acid and fatty alcohol and/or mixed esters of fatty acids containing 6 to 22 carbon atoms, methyl glucose and polyols, preferably glycerol or polyglycerol,

(13) polyalkylene glycols and

(14) glycerol carbonate.

The addition products of ethylene oxide and/or propylene oxide with fatty alcohols, fatty acids, alkylphenols, glycerol mono- and diesters and sorbitan mono- and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out.

Ethoxylated glycerides according to the invention are preferably a mixture of compounds of the following formula

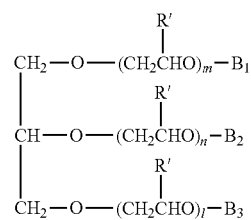

wherein

R' represents H or $CH_3$;

each m, n, and l independently represent a number from 0 to 40; the sum of m, n and l being in the range of 1 to 100, preferably 1 to 20, and said mixtures comprising (i) compounds represented by formula (I), where one of B1, B2 and B3 represents an acyl group having 6 to 22 carbon atoms, the remainder representing H;

(ii) compounds represented by formula (I), where two of B1, B2 and B3, independently, represent an acyl group having 6 to 22 carbon atoms, the remainder representing H;

(iii) compounds represented by formula (I), where each B1, B2 and B3, independently, represent an acyl group having 6 to 22 carbon atoms;

(iv) compounds represented by formula (I), where each of B1, B2 and B3 represent H; the weight ratio of the compounds (i)/(ii)/(iii) being 46-90/9-35/1-15. Particularly preferred are compounds of the formula III wherein the weight ratio (i)+(ii)+(iii)/(iv) is in the range of 85/15 to 40/60, more preferably in the range 80/20 to 45/55.

$C_{8-18}$ alkyl mono- and oligoglycosides, their production and their use as surfactants are known from the art. They are produced in particular by reaction of glucose or oligosaccharides with primary alcohols containing 8 to 18 C atoms. So far as the glycoside component is concerned, both monoglycosides, in which a cyclic sugar unit is attached to the fatty alcohol by a glycoside linkage, and oligomeric glycosides with a degree of oligomerization of preferably up to about 8 are suitable. The degree of oligomerization is a statistical mean value on which a homolog distribution typical of such technical products is based.

Zwitterionic surfactants may also be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known by the CTFA name of Cocamidopropyl Betaine is particularly preferred. Other suitable emulsifiers are ampholytic surfactants. Ampholytic surfactants are surface-active compounds which, in addition to a C8-18 alkyl or acyl group, contain at least one free amino group and at least one —COOH or —$SO_3H$ group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12-18}$ acyl sarcosine. Suitable anionic emulsifiers are, in particular, alkyl (ether) sulfates, acyl glutamates, protein fatty acid condensates and monoglyceride sulfates. Besides ampholytic emulsifiers, quaternary emulsifiers may also be used, those of the esterquat type, preferably methyl-quaternized difatty acid triethanolamine ester salts, being particularly preferred.

Suitable oil components are, for example, Guerbet alcohols based on fatty alcohols containing 6 to 18 and preferably 8 to 10 carbon atoms, esters of linear $C_6$-$C_{22}$ fatty acids with linear $C_6$-$C_{22}$ fatty alcohols, esters of branched $C_6$-$C_{13}$ carboxylic acids with linear $C_6$-$C_{22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl cleats, erucyl behenate and erucyl erucate. Also suitable are esters of linear $C_6$-$C_{22}$ fatty acids with branched alcohols, more particularly 2-ethyl hexanol, esters of hydroxycarboxylic acids with linear or branched $C_6$-$C_{22}$ fatty alcohols, more especially Dioctyl Malate, esters of linear and/or branched fatty acids with polyhydric alcohols for example propylene glycol, dimer diol or trimer triol) and/or Guerbet alcohols, triglycerides based on $C_6$-$C_{10}$ fatty acids, liquid mono-/di-/triglyceride mixtures based on $C_6$-$C_{18}$ fatty acids, esters of $C_6$-$C_{22}$ fatty alcohols and/or Guerbet alcohols with aromatic carboxylic acids, more particularly benzoic acid, esters of $C_6$-$C_{12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_6$-$C_{22}$ fatty alcohol carbonates, Guerbet carbonates, esters of benzoic acid with linear and/or branched $C_6$-$C_{22}$ alcohols, linear or branched, symmetrical or non-symmetrical dialkyl ethers containing 6 to 22 carbon atoms per alkyl group, ring opening products of epoxidized fatty acid esters with polyols, silicone oils and/or aliphatic or naphthenic hydrocarbons, for example squalane, squalene or dialkyl cyclohexanes.

Suitable secondary consistency factors are hydroxyfatty alcohols, partial glycerides, fatty acids or hydroxyfatty acids. Suitable thickeners are, for example, Aerosil types (hydrophilic silicas), polysaccharides, more particularly xanthan gum, guar guar, agar agar, alginates and tyloses, carboxymethyl cellulose and hydroxyethyl cellulose, relatively high molecular weight polyethylene glycol monoesters and diesters of fatty acids, polyacrylates (for example Carbopols or Synthalens), polyacrylamides, polyvinyl alcohol and polyvinyl pyrrolidone, surfactants such as, for example, ethoxylated fatty acid glycerides, esters of fatty acids with polyols such as, for example, pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400, cationic starch, copolymers of diallyl ammonium salts and acrylamides, quaternized vinyl pyrrolidone/vinyl imidazole polymers such as, for example, Luviquat (BASF), condensation products of polyglycols and amines, quaternized collagen polypeptides such as, for example, Lauryidimonium Hydroxypropyl Hydrolyzed Collagen, quaternized wheat polypeptides, polyethyleneimine, cationic silicone polymers such as, for example, Amodimethicone, copolymers of adipic acid and dimethylamino-hydroxypropyl diethylenetriamine (Cartaretine, Sandoz), copolymers of acrylic acid with dimethyl diallyl ammonium chloride, polyaminopolyamides and crosslinked water-soluble polymers thereof, cationic chitin derivatives such as, for example, quaternized chitosan, optionally in micro-crystalline distribution, condensation products of dihaloalkyls, for example dibromobutane, with bis-dialkylamines, for example bis-dimethylamino-1,3-propane, cationic guar gum such as, for example, Jaguar CBS, Jaguar C-17, Jaguar C-16 of Celanese, quaternized ammonium salt polymers such as, for example, Mirapol A-15, Mirapol AD-1, Mirapol AZ-1 of Mirapol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl, acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Preferred silicone compounds are hydrophobic silicone oils, which are silicone oils which are soluble in paraffinic oil at 25° C. Hydrophobic silicone oils to be used according to the present invention include both volatile and non-volatile silicone oils.

Specific examples include a cyclic methyl siloxane having the formula $\{(CH_3)_2SiO\}_x$ in which x is 3-6, or short chain linear methyl siloxanes having the formula $((CH_3)_2SiO\{(CH_3)_2SiO\}_ySi(CH_3)_3$ in which y is 0-5.

Some suitable cyclic methyl siloxanes are hexamethylcyclotrisiloxanes ($D_3$), a solid with a boiling point of 134° C. and the formula $\{(Me_2)SiO\}_3$; octamethylcyclotetrasiloxane (D4) with a boiling point of 176° C., a viscosity of 2.3 mm²/s, and the formula $\{(Me_2)SiO\}_4$; decamethylcyclopentasiloxane ($D_5$) (cyclomethicone) with a boiling point of 210° C., a viscosity of 3.87 mm²/s, and the formula $\{(Me_2)SiO\}_5$; and dodecamethylcyclohexasiloxane ($D_E$) with a boiling point of 245° C., a viscosity of 6.62 mm²/s and the formula $\{(Me_2)SiO\}_6$.

Some suitable short linear methyl siloxane are hexamethyldisiloxane (MM) with a boiling point of 100° C., viscosity of 0-65 mm²/s, and formula $Me_3SiOMe_3$; octamethyltrisiloxane (MDM) with a boiling point of 152° C., viscosity of 1.04 mm²/s, and formula $Me_3SiOMe_2SiOSiMe_3$; decamethyltetrasiloxane (MD2M) with a boiling point of 194° C., viscosity of 1.53 mm²/s, and formula $Me_3SiO(MeSiO)_2SiMe_3$; dodecamethylpentasiloxane (MD3M) with a boiling point of 229° C., viscosity of 2.06 mm²/s, and formula $Me_3SiO(Me_2SiO)_3SiMe_3$; tetradecamethylhexasiloxane (MD4M) with a boiling point of 245° C., viscosity of 2.63 mm²/s, and formula $Me_3SiO(Me_2SiO)_4SiMe_3$; and hexadecamethylheptasiloxane (MD5M) with a boiling point of 270° C., viscosity of 3.24 mm²/s, and formula $Me_3SiO(Me_2SiO)_5SiMe_3$.

Furthermore, long chain linear siloxanes such as phenyltrimethicone, bis(phenylpropyl)dimethicone, dimethicone, and dimethiconol are also included.

Typical examples of fats are glycerides while suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes, microwaxes; chemically modified waxes (hard waxes) such as for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Suitable deodorizers are, for example, antiperspirants, such as aluminium chlorhydrates. These antiperspirants are colorless hygroscopic crystals which readily deliquesce in air and which accumulate when aqueous aluminium chloride solutions are concentrated by evaporation. Besides the chlorhydrates, aluminium hydroxylactates and acidic aluminium/zirconium salts may also be used. Other suitable deodorizers are esterase inhibitors, preferably trialkyl citrates, such as trimethyl citrate, tripropyl citrate, triisopropyl citrate, tributyl citrate and, in particular, triethyl citrate. Esterase inhibitors inhibit enzyme activity and thus reduce odor formation. The free acid is probably released through the cleavage of the citric acid ester, reducing the ph value of the skin to such an extent that the enzymes are inhibited. Other esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester. Antibacterial agents which influence the germ flora and destroy or inhibit the growth of perspiration-decomposing bacteria, may also be present in stick products. Examples of such antibacterial agents are chitosan, phenoxyethanol and chlorhexidine gluconate. 5-Chloro-2-(2,4-dichlorophenoxy)-phenol.

Suitable antidandruff agents are climbazol, octopirox and zinc pyrithione. Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. Suitable swelling agents for aqueous phases are montmorillonites, clay minerals, Pemulen and alkyl-modified Carbopol types (Goodrich).

Examples of UV protection factors include organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomethyl ester;

derivatives of benzophenone, preferably 2-hydroxy-4-methoxybenzo-phenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone;

propane-1,3-diones such as, for example, 1-(4-tert.butylphenyl)-3-(4T-methoxyphenyl)-propane-1,3-dione;

2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example 1-(4'-tert.butylphenyl)-3-(4'-methoxyphenyl)-propane-1,3-dione, 4-tert-butyl-4'-methoxydibenzoylmethane (Parsol 1789) or 1-phenyl-3-(4'-isopropylphenyl)-propane-1,3-dione.

The UV-A and UV-B filters may of course also be used in the form of mixtures. Besides the soluble substances mentioned, insoluble pigments, i.e. finely dispersed metal oxides or salts, may also be used for this purpose. Examples of suitable metal oxides are, in particular, zinc oxide and titanium dioxide and also oxides of iron, zirconium, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have an average diameter of less than 100 nm, preferably from 5 to 50 nm and more preferably from 15 to 30 nm. They may be spherical in shape although ellipsoidal particles or other non-spherical particles may also be used. The pigments may also be surface-treated, i.e. hydrophilicized or hydrophobicized. Typical examples are coated titanium dioxides such as, for example, Titandioxid T 805 (Degussa) or Eusolex T2000 (Merck). Suitable hydrophobic coating materials are, above all, silicones and especially trialkoxyoctyl silanes or simethicones. So-called micro- or nanopigments are preferably used in sun protection products. Micronized zinc oxide is preferably used.

Besides the two above-mentioned groups of primary protection factors, secondary protection factors of the antioxidant type may also be used. Secondary sun protection factors of the antioxidant type interrupt the photochemical reaction chain which is initiated when UV rays penetrate into the skin. Typical examples of suitable antioxidants are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (also (metal) chelators (for example (α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, (α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxy-butyrophenone, uric acid and derivatives thereof, mannose and derivatives thereof, Superoxid-Dismutase, zinc and derivatives thereof (for example ZnO, ZnSO$_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

In addition, hydrotropes such as, for example, ethanol, isopropyl alcohol or polyols may be used to improve flow behavior. Suitable polyols preferably contain 2 to 15 carbon atoms and at least two hydroxyl groups. The polyols may contain other functional groups, especially amino groups, or may be modified with nitrogen. Typical examples are alkylene glycols such as, for example, ethylene glycol, diethylene glycol, propylene glycol, butylene glycol, hexylene glycol and polyethylene glycols having an average molecular weight of 100 to 1,000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms such as, for example, sorbitol or mannitol;

sugars containing 5 to 12 carbon atoms such as, for example, glucose or sucrose;

aminosugars such as, for example, glucamine;

dialcoholamines, such as diethanolamine or 2-aminopropane-1,3-diol.

Suitable preservatives are, for example, phenoxyethanol, formaldehyde solution, parabens, pentanediol or sorbic acid. Suitable insect repellents are N,N-diethyl-m-toluamide, pentane-1,2-diol or Insect Repellent 3535. A suitable self-tanning agent is dihydroxyacetone.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert-butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, filial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. The following are preferably used either individually or in the farm of mixtures: bergamot oil, dihydromyrcenol, lilial, lyral, citronellol, phenylethyl alcohol, α-nexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Typical examples of germ inhibitors are preservatives which act specifically against gram-positive bacteria such as, for example, 2,4,4'-trichloro-2'-hydroxydiphenyl ether, chlorhexidine (1,6-di-(4-chlorophenyl-biguanido)-hexane) or TCC (3,4,4'-trichlorocarbanilide). Numerous perfumes and essential oils also have antimicrobial properties. Typical examples are the active substances eugenol, menthol and thymol in clove, mint and thyme oil. The percentage content of the additional germ-inhibiting agents is normally about 0.1 to 2% by weight, based on the solids component of the preparations.

The Dyeing Compositions

The present invention also provides dyeing compositions comprising
a) a dyestuff; and
b) a mixture of amides, said mixture comprising, based on the total amount of the amide mixture:
i) 5-100 wt. %, preferably 30-70 wt. % of amides (a) according to the invention.
ii) 0-95 wt. %, preferably 20-80 wt. % of amides (b) according to the invention.

Particularly preferred dyeing compositions comprise:
a) a dyestuff; and
b) a mixture of amides of formula (II),

$$RO(CH_2CH_2O)_n—CH_2—CO—NH—R_4 \quad (II)$$

wherein
$R_4$ represents an hydroxyethyl, n-hydroxypropyl or iso-hydroxypropyl group, preferably hydroxyethyl group;
n has a value in the range of 0.2 to lower than 3, preferably in the range of 0.5 to 2.5, more preferably in the range of 1 to 2;
said mixture comprising, based on the total amount of the amide mixture:
i) 5-100 wt. %, preferably 20-70 wt. % of amides (a) of formula (II) wherein
R represents a $C_6$-$C_{24}$, preferably a $C_8$-$C_{18}$, more preferably a $C_{10}$-$C_{14}$ alkyl or alkenyl group having even number of carbon atoms and at least a 95 wt. % of linearity, preferably at least a 98 wt. % of linearity; and
ii) 0-95 wt. %, preferably 30-80 wt. % of amides (b) of formula (II) wherein
R represents a $C_5$-$C_{23}$, preferably a $C_5$-$C_{17}$, more preferably a $C_9$-$C_{15}$ alkyl or alkenyl group having odd or odd and even number of carbon atoms and a 40-85 wt. % of linearity, preferably a 45-75 wt. % of linearity, even more preferred a 55-75 wt. % of linearity.

The dyestuff can be a direct dye or a combination therefore. Examples of direct dyes include Acid Yellow 1 (C.I. 10316), Acid Yellow 3 (C.I. 47005), Acid Orange 7 (C.I. 15510), Acid Orange 87 (C.I. 45380:2), Acid Red 33 (C.I. 17200), Acid Violet 43 (C.I. 60730), Acid Blue 9 (C.I. 42090), Acid Green 25 (C.I. 61570), Acid Black 1 (C.I. 20470), Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 22 (C.I. 11055), Basic Red 51 (CAS RN 77061-58-9), Basic Red 76 (C.I. 12245), Basic Red 118 (C.I. 12251:1), Basic Yellow 57 (C.I. 12719), Basic Yellow 87 (CAS RN 68259-00-7), and Basic Orange 31 (CAS RN 97404-02-9)

If a single direct dye is used, it is preferably added in an amount of 0.01 to 20 wt. %, more preferably 0.05 to 10 wt. %, especially 0.1 to 5 wt. % on the basis of the entirety of the composition (after mixing of all the parts when a two-part or three-part composition is employed; this will apply equally hereinafter). When another direct dye is used in combination with the first one, the content of it in combination with the first direct dye preferably ranges from 0.05 to 10 wt. %, especially 0.1 to 5 wt. %, based on the whole composition.

The amount of the mixture of amides according to the invention to be added to compositions for dyeing keratinous fibres depends on several factors. Generally, the amount of the mixture of amides according to the invention is preferably between 0.05 wt. % to 25 wt. %, more preferably between 1 and 20 wt. %, even more preferably between 2.5 and 15 wt. % with respect to the total weight of the dyeing composition. In the case of two-part permanent hair dye compositions, the mixture of amides according to the invention can be present in both parts. However, it is preferably present in the part containing the dyestuff, preferably in an amount of 0.1 to 30 wt. % and more preferably 2.5 to 20 wt. % with respect to the weight of said part of the composition.

The weight ratio of the mixture of amides according to the invention (component b)) to dyestuff (component a)) is preferably in the range of 3:1 to 20:1, more preferably 4:1 to 15:1.

The hair dye composition of the present invention is preferably adjusted to pH 7 to 12, with pH 9 to 12 being more preferred. Buffering agents may be present in the compositions of the present invention in order to adjust the pH.

Suitable buffering agents are ammonium hydroxide, urea, ethylamine, dipropylamine, triethylamine and alkanediamines such as 1,3-diaminopropane, anhydrous alkaline alkanolamines such as, mono or di-ethanolamine, preferably those which are completely substituted on the amine group such as dimethylaminoethanol, polyalkylene polyamines such as diethylenetriamine or a heterocyclic amine such as morpholine as well as the hydroxides of alkali metals, such as sodium and potassium hydroxide, hydroxides of alkali earth metals, such as magnesium and calcium hydroxide, basic amino acids such as L-arginine, lysine, oxylysine and histidine and alkanolamines such as dimethylaminoethanol and aminoalkylpropanediol and mixtures thereof. Also suitable for use herein are compounds that form bicarbonate ($HCO_3^-$) by dissociation in water. Examples of suitable ion forming compounds are $Na_2CO_3$, $NaHCO_3$, $K_2CO_3$, $(NH_4)_2CO_3$, $NH_4HCO_3$, $CaCO_3$ and $Ca(HCO_3)_2$ and mixtures thereof.

Preferred for use as a buffering agent for the colouring compositions according to the present invention are ammonia, ammonium hydroxide, alkanolamides as monoethanolamide and/or sodium hydroxide.

The buffering agent is preferably added in an amount of 0.01 to 20 wt. %, more preferably 0.1 to 10 wt. %, especially 0.5 to 8 wt. % based on the whole composition.

In the hair dye composition of the present invention, an oxidizing agent can be incorporated. In this case, hair dyeing and bleaching can be carried out simultaneously, which facilitates more vivid hair dyeing. Ordinarily employed oxidizing agents, for example, hydrogen peroxide, persulfates such as ammonium persulfate, potassium persulfate and sodium persulfate, perborates such as sodium perborate, percarbonates such as sodium percarbonate and bromates such as sodium bromate and potassium bromate are usable. Out of them, hydrogen peroxide is especially preferred. The oxidizing agent is added in an amount of 0.5 to 10 wt. %, especially 1 to 8 wt. %, on the basis of the entirety of the composition.

Since the stability of hydrogen peroxide solutions is influenced primarily by the temperature and the pH value; hydrogen peroxide is stable in the pH range from 2 to 5, it is necessary to use a buffering agent having a pH within this range. Dilute acids are suitable hydrogen peroxide buffering agents. Phosphoric acid is a preferred agent for buffering hydrogen peroxide solutions.

This pH adjustment can be effected by using well known acidifying agents in the field of treating keratinous fibers, and in particular human hair, such as inorganic and organic acids such as hydrochloric acid, tartaric acid, citric acid, phosphoric acid and carboxylic or sulphonic acids such as ascorbic acid, acetic acid, lactic acid, sulphuric acid, formic acid, ammonium sulphate and sodium dihydrogenphosphate/phosphoric acid, disodium hydrogen phosphate/phosphoric acid, potassium chloride/hydrochloric acid, potassium dihydrogen phthalate/hydrochloric acid, sodium citrate/hydrochloric acid, potassium dihydrogen citrate/hydrochloric acid, potassium dihydrogencitrate/citric acid, sodium citrate/citric acid, sodium tartarate/tartaric acid, sodium lactate/lactic acid, sodium acetate/acetic acid, disodium hydrogenphosphate/citric acid and sodium chloride/glycine/hydrochloric acid and mixtures thereof.

Furthermore, the hair dye composition of the present invention may contain an oxidation dye. The incorporation of an oxidation dye enables markedly vivid dyeing not attainable by the single use of a direct dye. As the oxidizing agent, the above-exemplified oxidizing agents can be used, with hydrogen peroxide being particularly preferred. Alternatively, an oxidizing enzyme such as lactase can be employed. For the oxidation dye, known primary intermediates (developers) and couplers ordinarily employed for an oxidation type hair dye can be used.

The chemistry of oxidation dyeing involves a series of consecutive and competing reactions between hydrogen peroxide, primary intermediates (developers) and couplers. By appropriate selection of individual precursors, and adjustment of their absolute and relative concentrations, the formulator can produce a range of shades. By adjusting the ratio of peroxide to dye precursors, the colour of the hair can be changed from its natural tone to one which is lighter, darker, or similar in depth.

Examples of the developer include p-phenylenediamines having one or several groups selected from $NH_2$-, NHR- and $NR_2$-groups (R represents a C(1-4) alkyl or hydroxyalkyl group) such as p-phenylenediamine, p-toluoylenediamine, toluene-2,5-diamine, toluene-3,5-diamine N-methyl-p-phenylenediamine, chloro-p-phenylenediamine, 2-(2'-hydroxyethylamino)-5-aminotoluene, N,N-bis-(2-hydroxyethyl)-p-phenylenediamine, 2-hydroxyethyl-p-phenylenediamine, 2,6-dimethyl-p-phenylenediamine, methoxy-n-phenylenediamine, 2,6-dichloro-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine and N-2-methoxyethyl-p-phenylenediamine; 2,5-diaminopyridine derivatives and 4,5-diaminopyrazole derivatives; 2,5-diaminotoluene; p-aminophenols such as p-aminophenol, 2-methyl-4-aminophenol, N-methyl-p-aminophenol, 3-methyl-4-aminophenol, 2,6-dimethyl-4-aminophenol, 3,5-dimethyl-4-aminophenol, 2,3-dimethyl-4-aminophenol and 2,5-dimethyl-4-aminophenol; o-aminophenols, o-phenylenediamines, 4,4'-diaminophenylamine and hydroxypropylbis(N-hydroxyethyl-p-phenylenediamine); and salts thereof.

Examples of the coupler include hydroquinone, 1-naphthol, 1,5-dihydroxynaphthalene, 1,7-dihydroxynaphthalene, 2,7-dihydroxynaphthalene, 5-amino-2-methylphenol, 5-(2'-hydroxyethylamino)-2-methylphenol, 2,4-diaminoanisole, m-toluoylenediamine, resorcinol, m-phenylenediamine, m-aminophenol, o-aminophenol, 4-chlororesarcinol, 2-methylresorcinol, 2,4-diaminophenoxyethanol, 2,6-diaminopyridine, 2-amino-3-hydroxypyridine, 4-hydroxyindole, 6-hydroxyindole, 2-hydroxybenzodioxane, 2,5-dihydroxypyridine, 2,4-diamino-6-hydroxypyrimidine, 2,4,6-triaminopyrimidine, 2-amino-4,6-dihydroxypyrimidine, 4-amino-2,6-dihydroxypyrimidine, 4,6-diamino-2-hydroxypyrimidine, 2,6-diaminopyridine, 4-methyl-5-aminophenol, 4-methyl-5-(2-hydroxyethyl)aminophenol, 6-hydroxybenzomorpholine, 3,3'-dihydroxydiphenylamine, and 1,3-bis(2,4-diaminophenoxy)propane; and salts thereof. As a developer or coupler, at least one of the above-exemplified ones can be used. Although no particular limitation is imposed on its content, it is added in an amount of 0.01 to 20 wt. %, especially 0.5 to 10 wt. % based on the whole composition.

The viscosity of the dye solution is preferably in the range of 20 to 50,000 mPa·s, whereas the viscosity of the developer solution is preferably in the range of 4 to 25,000 mPas. After mixing, the combined solution has preferably a viscosity in the range of 2,000 to 50,000 mPa·s, more preferably 5,000 to 40,000 mPa·s. The same viscosities are preferred for single-component hair dyeing compositions.

To the hair dye composition of the present invention, a known auto-oxidation dye typified by an indole or an indoline, or a known direct dye such as a nitro dye or a disperse dye can also be added. Addition of a polyol, polyol alkyl ether, cationic or amphoteric polymer or silicone to the hair dye composition of the present invention is preferred, because the resulting hair dye composition has improved cosmetic effects.

In addition to the above-described components, those ordinarily employed as a raw material for cosmetics can be added to the hair dye composition of the present invention, within an extent not impairing the advantages of the present invention. Examples of such an optional component include hydrocarbons, animal or vegetable fats and oils, higher fatty acids, organic solvents, penetration promoters, cationic surfactants, natural or synthetic polymers, higher alcohols, ethers, amphoteric surfactants, nonionic surfactants, protein derivatives, amino acids, antiseptics, chelating agents, stabilizing agents, antioxidants, plant extracts, crude drug extracts, vitamins, ceramides, pseudoceramides, colourants, perfumes and ultraviolet absorbers.

The composition for dyeing keratinous fibres of the present invention can be prepared in a conventional manner into a one-part composition, a two-part composition having a first-part component containing an alkali agent and a second-part component containing an oxidizing agent, or a third-part composition having, in addition to these two components, a powdery oxidizing agent such as persulfate. The direct dye can be incorporated in either one or both of these components of the two-part or three-part composition. The one-part type is applied to the hair directly, while the two- or three-part type is applied to the keratinous fibres after mixing these parts upon hair dyeing.

No particular limitation is imposed on the form of the composition for dyeing keratinous fibres of the present invention. Examples include powder, transparent liquid, emulsion, cream, mousse, gel, paste, aerosol, and aerosol foam. It preferably has a viscosity of 2,000 to 100,000 mPa·s in the stage of application to the hair (after mixing of all the parts when a two-part or three-part type composition is employed).

Temporary hair colouring compositions, semi permanent hair colouring compositions and permanent hair colouring compositions comprising the mixture of amides according to the invention are also included in the subject of the present invention.

A method for dyeing keratinous fibres, preferably human hair, comprising applying to such fibres, an effective amount of at least one composition of the present invention, is also included in the subject of the present invention.

The use of the mixture of amides according to the invention as levelling agent in compositions for dyeing keratinous fibres, preferably human hair, is also included in the subject of the present invention.

The use of the mixture of amides according to the invention as thickening agent in compositions for dyeing keratinous fibres, preferably human hair, is also included in the subject of the present invention.

The following examples are given in order to provide a person skilled in the art with a sufficiently clear and complete explanation of the present invention, but should not be considered as limiting of the essential aspects of its subject, as set out in the preceding portions of this description.

EXAMPLES

Preparation of the Hair Dyes Compositions

In a manner known per se in the art, hair dye compositions as shown in Table 1 were prepared for the levelling agent according to the invention and for the comparative experiments.

The data appearing in each of the following tables represents weight percentage (wt. %).

TABLE 1

|  | Components | Quantity |
| --- | --- | --- |
| 1st part (dye solution) | Polyoxyethylene (13) Oleyl Ether | 10.00 |
|  | Oleic Acid | 10.00 |
|  | Amide/Mixture of amides | 15.00 |
|  | Monoethanolamine | 7.50 |
|  | Ethanol | 10.00 |
|  | Toluene-2,5-diamine | 0.61 |
|  | 1,3-Benzenediol (resorcinol) | 0.55 |
|  | Sodium Sulfite | 0.50 |
|  | Ascorbic Acid | 0.50 |
|  | Tetrasodium ethylendiaminetetraacetate | 0.50 |
|  | Deionized water | Balance |
| 2nd part (developer solution) | 50 wt. % aqueous hydrogen peroxide | 12.00 |
|  | Cetyl Alcohol | 2.00 |
|  | Glycerin | 1.00 |
|  | Dialkyldimethyl ammonium chloride | 1.00 |
|  | Behentrimonium Chloride | 3.00 |
|  | Phosphoric acid | Amount to adjust pH to 3.5 |
|  | Deionized water | Balance |

Evaluation of the Levelling Effect

For the preparation of the damaged hair, yak tresses (white colour) were treated with a hydrogen peroxide solution.

An aqueous solution of hydrogen peroxide ($H_2O_2$) at 6 wt. % was prepared and adjusted at approx. pH 9 with ammonia. 700 mL of this solution were placed into a crystal vessel and was heated at 32° C. Then yak tresses were introduced in this solution for 30 min. After that they were removed and rinsed with hot tap water (40° C.)

For each hair dye composition described before, having one part (dye solution) and second part (developer solution) were mixed at a weight ratio of 1:1 (the viscosity of said composition was measured with a Brookfield Viscometer LVD-VII+ (temperature=20° C.; spindle=3; speed 12 r.p.m.))

4 mL of the hair dye composition mixture was applied in each hair tress for 30 minutes at room temperature. 2 healthy yak tresses and 2 damaged yak tresses (treated with the hydrogen peroxide solution) were used. After that, each tress was rinsed with top water (1 min), washed with a standard shampoo (1 min), rinsed again with top water (1 min) treated with a standard hair conditioner (1 min, to detangle the hair tress), rinsed (1 min) again and dried over night at room temperature.

The intensity of the colour of hair tresses after the colouration treatment was determined with a spectrophotometer Spectraflash 600, supplied by DataColor (Illuminant: medium day light D65, 10° observer, % R SAV SCI UV Inc) using the CIE 1976-L*a*b* method.

The levelling effect (LE) of each amide or mixture of amides was calculated as follows:

LE=Δ$E$DH(colour intensity on damaged hair)–Δ$E$HH (colour intensity on healthy hair)

Representing ΔE the difference in colour between each tress before and after the treatment with the dyeing composition (colour intensity)

Smaller values of LE indicate the better levelling effect of the amide or mixture of amides.

Results, which are averages of values for 2 samples, each of which underwent 10 separate measurements, are indicated in Table 2.

Evaluation of the Yield Value

The yield value is defined as the minimum required force to initiate flow. There are several ways to measure a yield value.

The yield value of each hair dye composition described before, having one part (dye solution) and second part (developer solution) were mixed at a weight ratio of 1:1 was determined with a rheometer Haake RheoStress 600 supplied by Thermo electron corporation. A shear stress ramp from 0 to 100 Pa is applied on each sample at room temperature (20-25° C.) and measuring the resulting deformation. The measured results are represented in a graph where the x axis is the shear stress and the y axis is the deformation, two curve segments are observed. The first segment is a line with a slope of one: the sample is elastically deformed and the slope of shear stress versus deformation represents the "spring coefficient" of the fluid below its yield value. At the yield value the curve turns into its second segment: the slope angle changes much indicating the start of volume flow. Yield value is the crossing point of both tangents.

High values of yield value indicate that the sample doesn't leak once it is on hair. Typical values obtained from commercial products are between 5 to 35 Pa, better between 10 to 25 Pa.

Results are indicated in Table 2.

TABLE 2

| Examples | Amide or mixture of amides | Viscosity after 1 min (mPa·s) | Levelling effect (LE) | Yield value (Pa) | Colour intensity (ΔE (HH)) |
| --- | --- | --- | --- | --- | --- |
| 1 | Mixture (65:35 wt. %) of Polyoxyethylene (2) (45% linear) $C_{13}$-$C_{15}$ alkyl | 6290 | 1.50 | 16.37 | 42.00 |

TABLE 2-continued

| Examples | Amide or mixture of amides | Viscosity after 1 min (mPa·s) | Levelling effect (LE) | Yield value (Pa) | Colour intensity (ΔE (HH)) |
|---|---|---|---|---|---|
| | ether carboxylic acid monoethanolamide; and Polyoxyethylene (2) (≧98% linear) $C_{14}$ alkyl ether carboxylic acid monoethanolamide | | | | |
| 2 | Polyoxyethylene (2) (≧98% linear) oleyl ($C_{18:1}$) ether carboxylic acid monoethanolamide | 5759 | 0.9 | 15.77 | 44.5 |
| C-1 | Polyoxyethylene (2) (55% (50%) linear) $C_{13}$-$C_{15}$ alkyl ether carboxylic acid monoethanolamide | 4675 | 1.75 | 12.48 | 33.25 |
| C-2 | Polyoxyethylene (4.5) (≧98% linear) $C_{12}$-$C_{14}$ alkyl ether carboxylic acid monoethanolamide | 2980 | 1.25 | 1.8 | 34.50 |
| C-3 | Polyoxyethylene (7) (≧98% linear) $C_{12}$-$C_{14}$ alkyl ether carboxylic acid monoethanolamide | 602 | 1.60 | 2.7 | 33.90 |

These results clearly illustrate that the dyeing compositions according to the invention, exhibits unexpectedly higher colouring intensity on healthy hair (ΔE HH) than the comparative experiments C1-C3.

Furthermore, the dyeing compositions according to the invention exhibit better levelling effect (LE) in comparison to comparative experiment C1 and similar levelling effect (LE) in comparison to comparative experiments C1 and C3.

Finally, it is also remarked that the viscosity and the yield value of the dyeing compositions according to the invention, measured 1 minute after mixing the dye solution (first part) and the developer solution (second part), shows surprisingly higher values than the comparative experiments.

From the above, it is clear that the mixture of amides according to the invention can act as thickening agent in dyeing compositions.

Modifications, which do not affect, alter, change or modify the essential aspects of the compositions described, are included within the scope of the present invention.

The invention claimed is:

1. A mixture of amides of the following formula (I)

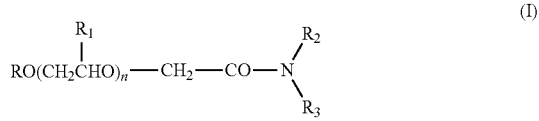

(I)

wherein
$R_1$ represents a hydrogen atom or an alkyl group having 1 to 5 carbon atoms;
$R_2$ and $R_3$ represent independently, a hydrogen atom or a linear or branched alkyl group having 1 to 5 carbon atoms which is optionally hydroxylated, provided that $R_2$ and $R_3$ are not a hydrogen atom at the same time;
n has a value in the range of 0.2 to lower than 3;
characterized in that said mixture comprises:
amides (a) of formula (I) wherein
R represents a $C_6$-$C_{24}$ alkyl or alkenyl group having an even number of carbon atoms and at least a 95 wt. % of linearity; and
amides (b) of formula (I) wherein
R represents a $C_5$-$C_{23}$ alkyl or alkenyl group having an odd or odd and even number of carbon atoms and a 35-85 wt. % of linearity.

2. The mixture of amides according to claim 1, wherein in the amides (a) of formula (I) R represents a $C_8$-$C_{18}$ alkyl or alkenyl group having an even number of carbon atoms and at least a 98 wt. % of linearity.

3. The mixture of amides according to claim 1, wherein in the amides (b) of formula (I) R represents a $C_5$-$C_{17}$ alkyl or alkenyl group having an odd or odd and even number of carbon atoms and a 40-75 wt. % of linearity.

4. The mixture of amides according to claim 1, wherein the weight ratio of amides (a) to amides (b) is in the range of 1:10 to 10:1.

5. The mixture of amides according to claim 4, wherein the weight ratio of amides (a) to amides (b) is in the range of 1:5 to 5:1.

6. The mixture of amides according to claim 1, wherein $R_2$ and $R_3$ represent independently, a hydrogen atom or a hydroxylated alkyl group having 1 to 5 carbon atoms selected from the group consisting of hydroxymethyl, hydroxyethyl, n-hydroxypropyl, iso-hydroxypropyl, n-hydroxybutyl, iso-ydroxybutyl, tert-hydroxybutyl and n-hydroxypentyl; provided that either $R_2$ or $R_3$ is not a hydrogen atom.

7. The mixture of amides according to claim 6, wherein $R_2$ represents a hydrogen atom or a hydroxyethyl group and $R_3$ represents a hydroxyethyl, n-hydroxypropyl or iso-hydroxypropyl group.

8. The mixture of amides according to claim 1 wherein $R_1$ represents a hydrogen atom, $R_2$ represents a hydrogen atom and $R_3$ represents a hydroxyethyl group.

9. A cosmetic composition comprising a mixture of amides according to claim 1.

10. A dyeing composition comprising
a) a dyestuff; and
b) a mixture of amides, said mixture comprising, based on the total amount of the amide mixture:
i) 5-100 wt. % of amides (a) as defined in claim 1, and ii) 0-95 wt. % of amides (b) as defined in claim 1.

11. The composition according to claim 10, wherein the weight ratio of amides (a) to amides (b) is in the range of 1:10 to 10:1.

12. The composition according to claim 10 comprising, based on the total amount of the amide mixture:
i) 20-70 wt. % of amides (a), and
ii) 30-80 wt. % of amides (b).

13. The composition according to claim 10, further comprising an oxidizing agent.

14. The composition according to claim 10 further comprising an oxidation dye.

15. The composition according to claim 10, wherein the mixture of amides is present in an amount of 0.05 to 25 wt. % with respect to the total weight of the composition.

16. A method for dyeing keratinous fibres comprising applying an effective amount of at least one composition according to claim 10 to keratinous fibres.

17. The method for dyeing keratinous fibres according to claim 16, wherein said keratinous fibres are human hair.

18. A composition for dyeing keratinous fibres comprising mixture of amides according to claim 1 as a levelling agent.

19. A composition for dyeing keratinous fibres comprising a mixture of amides according to claim 1 as a thickening agent.

20. The composition according to claim 19, wherein said keratinous fibres are human hair.

* * * * *

UNITED STATES PATENT AND TRADEMARK OFFICE
CERTIFICATE OF CORRECTION

| | | |
|---|---|---|
| PATENT NO. | : 8,246,697 B2 | Page 1 of 1 |
| APPLICATION NO. | : 13/141931 | |
| DATED | : August 21, 2012 | |
| INVENTOR(S) | : Jurgen Benade et al. | |

It is certified that error appears in the above-identified patent and that said Letters Patent is hereby corrected as shown below:

In the Claims

In Claim 6, Column 24, lines 39-40, the hydrogen atom or hydroxylated alkyl group reading "iso-ydroxybutyl" should read --iso-hydroxybutyl--.

In Claim 18, Column 26, lines 1-2, the claim reading "A composition . . . comprising mixture" should read --A composition . . . comprising a mixture--.

Signed and Sealed this
Thirtieth Day of July, 2013

Teresa Stanek Rea
*Acting Director of the United States Patent and Trademark Office*